(12) United States Patent
Cabibihan et al.

(10) Patent No.: US 10,810,405 B2
(45) Date of Patent: Oct. 20, 2020

(54) BIOMETRIC LIVENESS DETECTION THROUGH BIOCOMPATIBLE CAPACITIVE SENSOR

(71) Applicant: QATAR UNIVERSITY, Doha (QA)

(72) Inventors: John-John Cabibihan, Doha (QA); Kishor Kumar Sadasivuni, Doha (QA); Ahmad Yaser Alhaddad, Doha (QA)

(73) Assignee: QATAR UNIVERSITY, Doha (QA)

( * ) Notice: Subject to any disclaimer, the term of this patent is extended or adjusted under 35 U.S.C. 154(b) by 238 days.

(21) Appl. No.: 16/058,453

(22) Filed: Aug. 8, 2018

(65) Prior Publication Data

US 2019/0050622 A1    Feb. 14, 2019

Related U.S. Application Data (60) Provisional application No. 62/543,188, filed on Aug. 9, 2017.

(51) Int. Cl.
| | |
|---|---|
| *A61B 5/04* | (2006.01) |
| *G06K 9/00* | (2006.01) |
| *A61B 5/117* | (2016.01) |
| *A61B 5/024* | (2006.01) |

(52) U.S. Cl.
CPC ........ *G06K 9/0012* (2013.01); *A61B 5/02427* (2013.01); *A61B 5/04* (2013.01); *A61B 5/117* (2013.01); *G06K 9/0002* (2013.01)

(58) Field of Classification Search
CPC ..... G06F 21/32; A61B 5/02427; A61B 5/681; G06K 9/0002; G06K 9/0004
See application file for complete search history.

(56) References Cited

U.S. PATENT DOCUMENTS

| | | | |
|---|---|---|---|
| 5,953,441 | A | 9/1999 | Setlak |
| 6,665,428 | B1 | 12/2003 | Gozzini |

(Continued)

FOREIGN PATENT DOCUMENTS

| | | | | |
|---|---|---|---|---|
| CN | 102831410 | A | | 12/2012 |
| CN | 203689535 | U | | 7/2014 |
| CN | 204904295 | U | * | 12/2015 ............... G06K 9/00 |

OTHER PUBLICATIONS

Pryor, "Smart Stuff: A case study of a smart water bottle," in 2016 38th Annual International Conference of the IEEE Engineering in Medicine and Biology Society (EMBC), 2016, pp. 6307-6310. (Year: 2016).*

(Continued)

*Primary Examiner* — Yuzhen Shen
(74) *Attorney, Agent, or Firm* — Squire Patton Boggs (US) LLP (57) ABSTRACT

A method may include measuring, photoplethysmography (PPG) data and capacitance data of an object. The method may also include, with the PPG data and the capacitance data, detecting, by a microprocessor, positive peaks of the data by comparing successive measurements. The method may further include finding, by the microprocessor, a maximum peak value of the detected positive peaks, and generating, by the microprocessor, a threshold value based on detected positive peaks. If the maximum peak value is greater than the threshold value, analyze, by the microprocessor, a fingerprint of the object. The method may also include determining, by the microprocessor, based on the PPG data, the capacitance data and the fingerprint of the object, at least one of if the object is authorized or unauthorized, and if the object is a human being or not a human being.

8 Claims, 10 Drawing Sheets

(56) References Cited

U.S. PATENT DOCUMENTS

| | | | |
|---|---|---|---|
| 2014/0049373 A1 | 2/2014 | Troy et al. | |
| 2014/0368467 A1* | 12/2014 | Park | G06F 3/044 345/174 |
| 2015/0043792 A1* | 2/2015 | Nada | G06K 9/00006 382/126 |
| 2016/0154952 A1* | 6/2016 | Venkatraman | G06Q 20/3278 705/44 |
| 2016/0357296 A1* | 12/2016 | Picciotto | G06F 3/016 |

OTHER PUBLICATIONS

Aggarwal, T. et al., "Fake Fingerprint Detection Methods", IJITKM Special Issue (ICFTEM-2014) May 2014 pp. 61-69 (ISSN 0973-4414).

Karlsson, N. et al., "A Capacitive Sensor for the Detection of Humans in a Robot Cell", 1993 Instrumentation and Measurement Technology Conference, 1993. IMTC/93. Conference Record, IEEE DOI:10.1109/IMTC.1993.382659.

Ezhilarasan, A. G. M., "Spoof Detection of Fingerprint Biometrics based on Local and Global Quality Measures", International Journal of Computer Aplications (0975-8887), vol. 124, No. 16, Aug. 2015.

"Patented Live & Fake Finger Detection Technology", htttps://messe.nikkei.co.jp/files/SSI375/4-201401061400240475.pdf.

"FpSafe", http://www.novowave.co/#!about-fpsafe/c1y47.

"VIRDI Technology Patents", http://virdi.com/sg/biometric-technology-patents/.

"Liveness Detection to Fight Biometric Spoofing", http://blog.m2sys.com/scanning-and-efficiency/liveness-detection-fight-biometric-spoofing/.

* cited by examiner

BIOMETRIC LIVENESS DETECTION THROUGH BIOCOMPATIBLE CAPACITIVE SENSOR

CROSS REFERENCE TO RELATED APPLICATION

This application claims priority to U.S. Provisional Application No. 62/543,188 filed on Aug. 9, 2017. The entire contents of the above-referenced provisional application is hereby incorporated by reference.

FIELD OF INVENTION

Certain embodiments may generally relate to identification techniques. More specifically, certain embodiments may generally relate to identification techniques with biometric data, and may also generally relate to implementing biometric data in developing anti-spoofing methods and devices.

BACKGROUND OF THE INVENTION

Biometrics refers to the measurements done to identify a person through the analysis of biological data. Many aspects of human biology may be used as an identification marker such as fingerprints, iris, and retina. Other characteristics may include signatures or gait patterns. Biometrics, when combined with traditional security methods, have the potential to prevent unauthorized access to sensitive information or facilities. These may be capable of a high level of accuracy for identification, recognition, classification, and analysis.

Each person has a unique fingerprint pattern. With the advancement of pattern recognition algorithms, fingerprint scanners are being used in many fields such as a login method for computers and mobile devices, immigration, and national identification cards. Unlike traditional methods, biometric markers are more difficult to forge and cannot be easily replicated since they are a part of the human body.

A commonly used biometric system is the Automatic Fingerprint Identification System (AFIS). The AFIS was built based on the concept of careful visual inspection to identify the fingerprint using patterns. Fingerprint identification systems, while widely used, are also one of the easiest to spoof. Thus, there is a need to develop an easy-to-integrate and inexpensive method to enhance the security of fingerprint scanners.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

SUMMARY OF THE INVENTION

According to certain embodiments, a biometric scanner device may include an add-on part electrically integrated with the biometric scanner device, wherein the add-on part may include a capacitance sensor configured to measure a capacitance of an object. The biometric scanner device may also include a microprocessor electrically connected to the add-on part. The microprocessor may be configured to receive the capacitance measurement obtained from the capacitance sensor, analyze the capacitance measurement against a threshold capacitance, and determine, according to the analysis, at least one of if the object is authorized or unauthorized, and if the object is a human being or not a human being. The biometric scanner device may also include a screen to output the determination made by the microprocessor.

In an embodiment, the add-on part may include a pulse sensor configured to detect and measure a pulse of the object. In another embodiment, the microprocessor may be configured to verify the object based on the detected pulse. In an embodiment, the add-on part may include a foam layer disposed on a side of the capacitance sensor. According to an embodiment, the capacitance sensor may include a microcontroller configured to detect touch by measuring a change of capacitance of the object.

According to another embodiment, the capacitance sensor may include at least one integrated circuit and at least one passive component. In an embodiment, the capacitance sensor may include a high-frequency oscillator, an inverter, and a timing component.

According to certain embodiments, an anti-spoofing method may include measuring, with an add-on part comprising a photoplethysmography (PPG) sensor and a capacitance sensor, PPG data and capacitance data of an object. The method may also include, with the PPG data and the capacitance data, detecting, by a microprocessor, positive peaks of the data by comparing successive measurements. In addition, the method may include finding, by the microprocessor, a maximum peak value of the detected positive peaks. The method may also include generating, by the microprocessor, a threshold value based on detected positive peaks. If the maximum peak value is greater than the threshold value, the method may include analyzing, by the microprocessor, a fingerprint of the object. The method may further include determining, by the microprocessor, based on the PPG data, the capacitance data and the fingerprint of the object, at least one of if the object is authorized or unauthorized, and if the object is a human being or not a human being.

In an embodiment, the method may include checking all of the detected positive peaks for accurate signal determination, and plotting the PPG data and capacitance data. In another embodiment, if the maximum peak value is less than the threshold value, the method may include repeating the plotting the PPG data and the capacitance data, detecting positive peaks of the data, checking all of the detected positive peaks, finding the maximum peak value, and generating the threshold value. According to an embodiment, the method may further include detecting, with the capacitance sensor, touch of the object by measuring a change of capacitance of the object. According to another embodiment, the method may include converting, by the microprocessor, the change of capacitance of the object into a voltage output.

According to certain embodiments, there may be provided a computer program, embodied on a non-transitory computer readable medium. The computer program, when executed by a processor, causes the processor to perform the method described above. Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. The following detailed description is, therefore, not to be taken in a limiting sense.

DETAILED DESCRIPTION

The features, structures, or characteristics of the invention described throughout this specification may be combined in any suitable manner in one or more embodiments. For example, the usage of the phrases "certain embodiments," "some embodiments," or other similar language, throughout this specification refers to the fact that a particular feature, structure, or characteristic described in connection with the embodiment may be included in at least one embodiment of the present invention.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. The following detailed description is, therefore, not to be taken in a limiting sense.

The examples described herein are for illustrative purposes only. As will be appreciated by one skilled in the art, certain embodiments described herein, including, for example, but not limited to, those shown in FIGS. 1-10, may be embodied as a system, apparatus, method, or computer program product. Accordingly, certain embodiments may take the form of an entirely software embodiment or an embodiment combining software and hardware aspects. Software may include but is not limited to firmware, resident software, or microcode. Furthermore, other embodiments may take the form of a computer program product accessible from a computer-usable or computer-readable medium providing program code for use by or in connection with a computer or any instruction execution system.

Any combination of one or more computer usable or computer readable medium(s) may be utilized in certain embodiments described herein. For the purposes of this description, a computer-usable or computer readable medium can be any apparatus that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may independently be any suitable storage device, such as a non-transitory computer-readable medium. Suitable types of memory may include, but not limited to: a portable computer diskette; a hard disk drive (HDD), a random access memory (RAM), a read-only memory (ROM); an erasable programmable read-only memory (EPROM or Flash memory); a portable compact disc read-only memory (CDROM); and/or an optical storage device.

The memory may be combined on a single integrated circuit as a processor, or may be separate therefrom. Furthermore, the computer program instructions stored in the memory may be processed by the processor can be any suitable form of computer program code, for example, a compiled or interpreted computer program written in any suitable programming language. The memory or data storage entity is typically internal, but may also be external or a combination thereof, such as in the case when additional memory capacity is obtained from a service provider. The memory may also be fixed or removable.

The computer usable program code (software) may be transmitted using any appropriate transmission media via any conventional network. Computer program code, when executed in hardware, for carrying out operations of certain embodiments may be written in any combination of one or more programming languages, including, but not limited to, an object oriented programming language such as Java, Smalltalk, C++, C# or the like and conventional procedural programming languages, such as the "C" programming language or similar programming languages. Alternatively, certain embodiments may be performed entirely in hardware.

Depending upon the specific embodiment, the program code may be executed entirely on a device, partly on the device, as a stand-alone software package, partly on the device and partly on a remote computer, or entirely on the remote computer. In the latter scenario, the remote computer may be connected to the device through any type of conventional network. This may include, for example, a local area network (LAN) or a wide area network (WAN), Bluetooth, Wi-Fi, satellite, or cellular network, or the connection may be made to an external computer (for example, through the Internet using an Internet Service Provider).

In general, fingerprint scanning identification and verification may involve several stages. First, the fingerprint scanner may take an image of a user's unique fingerprint traits. While this image is saved later on in a database as a minutiae file, many fingerprint scanning systems face a challenge of acquiring high quality images of a fingerprint. In certain embodiments, the image quality may be measured in dots per inch (DPI). In order to have a higher resolution image the resolution may require having more dots per inch, while the standard fingerprinting scanning machines that use the forensic quality generally have an image of 500 DPI.

The initial process in fingerprint scanning technology is image processing, which may be done by converting the image into an available formatting data. Later on, the enhancement process may be taken into account in order to reduce distortion of the fingerprint image, caused by dry skin, sweat or dust. The final step in the process may identify and locate distinctive characteristics.

A normal finger scan may generate between 15 and 20 minutiae, in which a template may then be formed. This may be done by filtering, and mapping distortions and false minutiae where the defective minutiae may be filtered and carried out before a template is created. This process may be supported by specific algorithms in which it compares the enrollment template to the verification template. A smaller portion of the captured finger may also be used for pattern recognition purposes.

There have been documented ways and techniques to spoof fingerprint scanning devices. Due to these drawbacks, it is often desired to develop new security firewalls to minimize the risks. In general, fingerprint scanners may use a capacitive sensor to capture the finger image, but such sensors are still subjected to major and serious security hacks. Current finger scanners may take 2D images, which provide an easier way to fool finger scanners by placing an identical printed fingerprint image over the sensors' surface. Thus, it is desirable to prevent fake fingers from fooling commercially available fingerprint scanning devices.

Further, biometric systems inevitably analyze the unique behavioral signature of an individual, from which a verdict can be made to either confirm or determine that individual's identity since it is unique. Biometric aspects may be exclusive to an individual and it may simplify the authentication process by eliminating the need of a password and/or personal identification number (PIN). An anti-spoofing method is usually accepted to be a technique capable of automatically distinguishing between real biometric traits presented to the sensor and synthetically produced artifacts containing a biometric trait.

Biometric detection systems of certain embodiments may be applied in banking, and may provide methods of preventing fraud and illegal access of one's property, details, and accounts. In certain embodiments, fingerprints may be used as a biometric characteristic. Fingerprints may also be used for access control in, for example, access control concerning security sensitive environments such as access to protected facilities or sensitive data.

Spoofing generally refers to a fake access by an illegal or unauthorized user into the fingerprint biometric system using a fake fingerprint. Fake fingerprints may be derived from various materials such as clay, gelatin, silicon, and others. Security is often a focus in biometrics applications. Thus, correct authentication of enlisted fingerprints can be crucial for each system.

Figure 1:
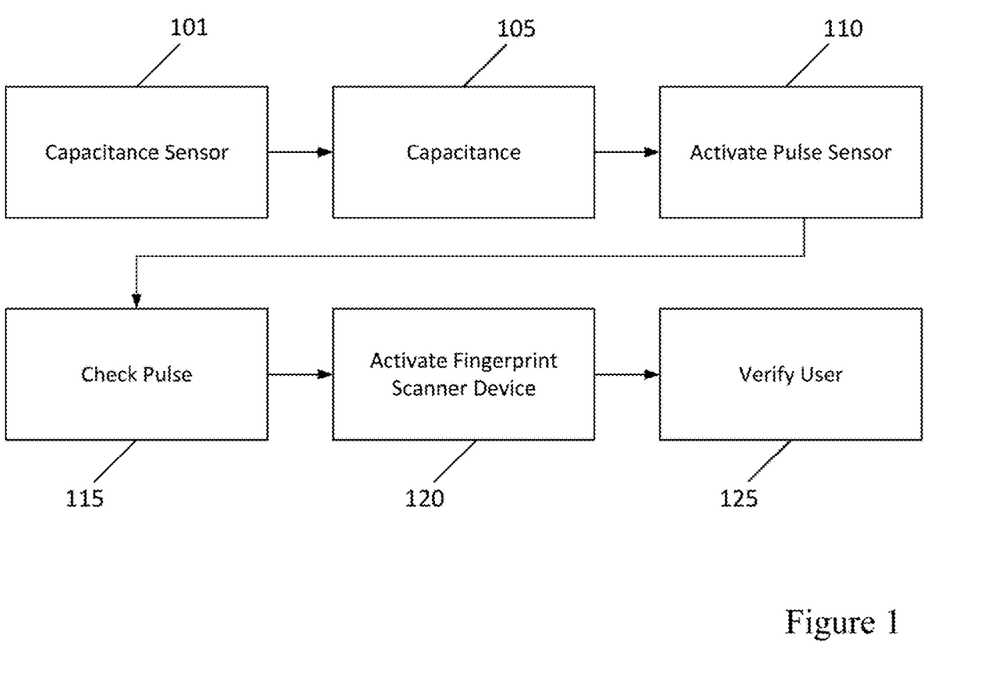
FIG. 1 illustrates an example working principle of an anti-spoofing device according to certain embodiments.

FIG. 1 illustrates an example working principle of an anti-spoofing device according to certain embodiments. In particular, FIG. 1 illustrates the working principle of an attachment device such as, for example, a capacitive sensor. Initially, the capacitive sensor 101 may detect the capacitance 105 of a human finger based on the capacitance change. This may activate a pulse sensor 110 to detect the pulse of the finger 115. Once the pulse sensor recognizes the pulse from the finger, the relay may open the electrical circuit, and the biometric device may read the fingerprint of the human subject 120 and proceed to verify the subject 125.

FIG. 2(A) illustrates a fingerprint scanner device 201 with one or more add-on parts 205 according to certain embodiments, and FIG. 2(B) illustrates a 3D design of the add-on part 205 according to certain embodiments. As illustrated in FIG. 2(A), an add-on part 205 may be integrated with the fingerprint scanner device or a biometric scanner device 201. The add-on part 205, according to an embodiment, may be made with strong insulation for the capacitance sensor. The add-on part 205 is not limited to being attached to and implemented with the fingerprint scanner device 201, and may in other embodiments, be attached to and implemented with various other biometric devices. Such other biometric devices may include, but not limited to BioLink FingerPass™, Well Tech Systems, Fulcrum biometric devices, and Cogent 3M CSD200 Biometric Devices.

According to certain embodiments, the add-on part 205 may be easily integrated with currently available biometric devices, and may include a capacitive sensor that is configured to differentiate between fingerprints of a fake finger and fingerprints of a real finger, and a pulse sensor for detecting and/or measuring the pulse from a human finger. The capacitive sensor and the pulse sensor may be integrated with the add-on part 205 by being disposed at a sensor bock 215 of the add-on part 205 located at an interior surface of the add-on part 205, as shown in FIG. 2(B). As also illustrated in FIG. 2(B), the add-on part 205 may include a hole 220 for cables that are attached to the capacitive sensor and the pulse sensor leading out to a microprocessor 210. Further, coaxial cables may be used to avoid the capacitive interference and the wire having two conductors separated by a dielectric (ceramic) material. In addition, a laminated shielding tap that includes plastic film may be covered around the cable.

As illustrated in FIG. 2(A), in certain embodiments, the add-on part 205 may be integrated with a microprocessor 210 to implement instructions received from the add-on part 205. According to certain embodiments, the instructions may be single cycle instructions. In other embodiments, a standalone Universal Serial Bus (USB) device interface may be used to integrate the add-on part 205 with the microprocessor 210. The device may also be designed to incorporate a flash memory for data acquisition and processing.

As noted above, the pulse sensor and the capacitive touch sensor may be embedded in the add-on part 205. The add-on part 205, in certain embodiments, may be a dome-shaped attachment of the fingerprint scanner device 201. In certain embodiments, the pulse sensor may be very sensitive to external light. Thus, a dome-shaped structure may be designed to overcome the pulse sensor's high sensitivity. In other embodiments, the dome-shaped structure of the add-on part 205 may be used to protect the scanning area of the fingerprint scanner device 201 from external elements.

Figure 2:
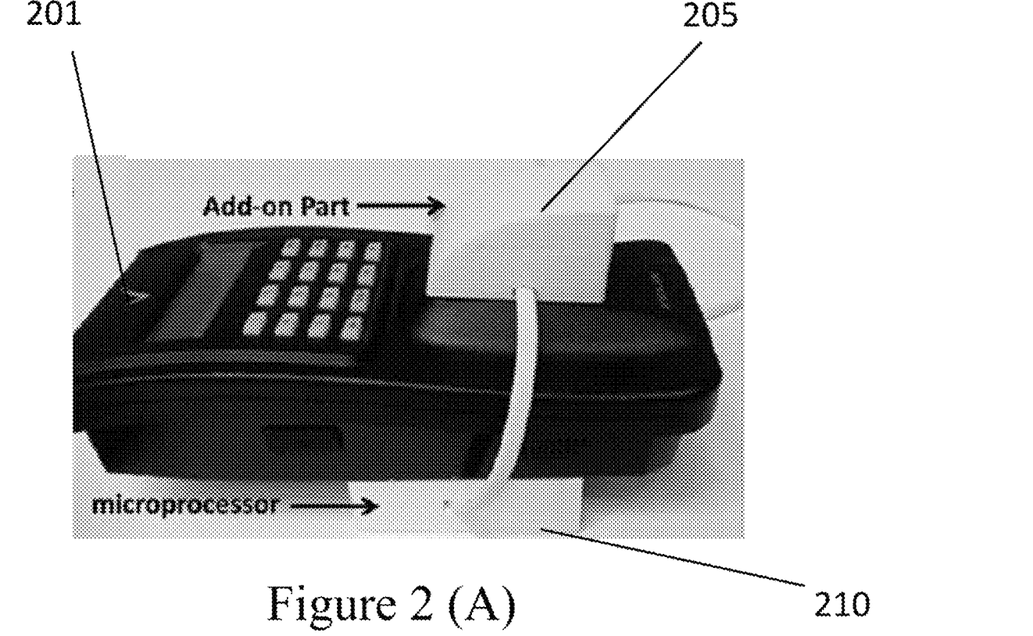
FIG. 2(A) illustrates a fingerprint scanner device with one or more add-on parts according to certain embodiments.
FIG. 2(B) illustrates a 3D design of the add-on part according to certain embodiments.
FIG. 2(C) illustrates the fingerprint scanner device with a fake finger according to certain embodiments.
FIG. 2(D) illustrates the fingerprint scanner device with a real finger according to certain embodiments.
Figure 2C:
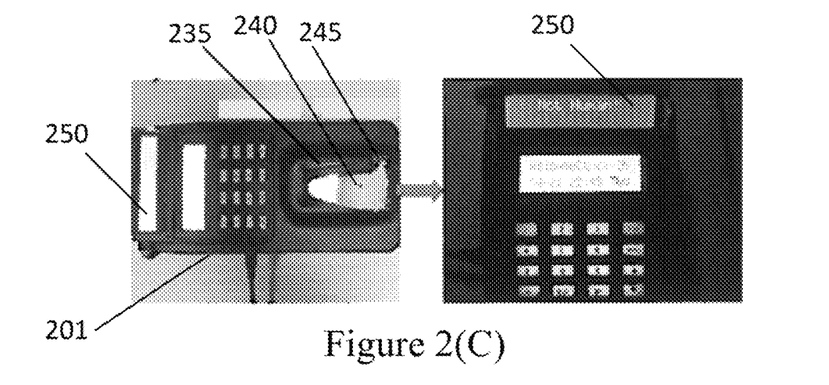

FIG. 2(C) illustrates the fingerprint scanner device 201 with a fake finger 240 according to certain embodiments. The fake finger 240 may be pressed upon a scanning surface of the optical scanner 235, and data related to the fake finger 240 may be collected and processed by the fingerprint scanner device 201. In addition to being scanned by the optical scanner 235, the capacitive sensor 245 measures a capacitance of the fake finger 240 to determine if the fake finger 240 is indeed a fake finger or if it is a finger of a real human being. Once the information of the fake finger 240 has been obtained from the optical scanner 235 and the capacitive sensor 245, a result is displayed on a display screen 250 of the fingerprint scanner device 201. For example, as shown in FIG. 2(C), if a fake finger 240 is used, the fingerprint scanner device 201 would return a result of "Not Human!."

Figure 2D:
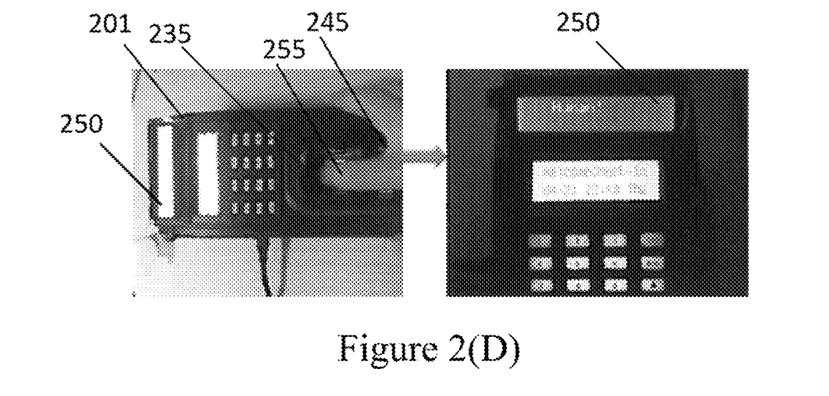

FIG. 2(D) illustrates the fingerprint scanner device 201 with a real finger 255 according to certain embodiments. The functionalities of the fingerprint scanner device 201 with the real finger 255 may be the same as that with the fake finger 240 described above. Further, with the real finger 255, once the information of the real finger 255 has been obtained from the optical scanner 235 and the capacitive sensor 245, a result may be displayed on the display screen 250 of "Human!", indicating that the real finger 255 is indeed a real finger.

Figure 3:
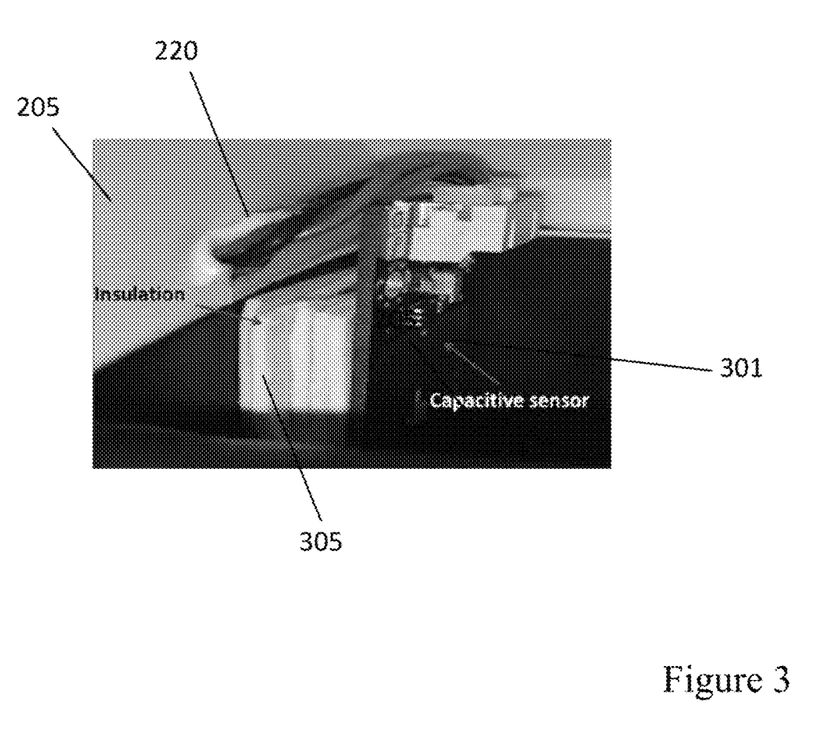
FIG. 3 illustrates an exemplary add-on part according to certain embodiments.

FIG. 3 illustrates an exemplary add-on part 205 according to certain embodiments. As illustrated in FIG. 3, the add-on part 205 may be of a dome shape. The add-on part 205 may also include the hole 220 shown in FIG. 2(B), and a capacitive sensor 301 embedded in the dome of the add-on part 205 according to certain embodiments. As shown in FIG. 3, foam 305 may be included as insulation on a side of the capacitive sensor 301 to prevent false positives from the capacitive sensor due to the capacitance stored in the dome. In an embodiment, the foam 305 may be disposed between a side of the capacitive sensor 301 and an inner wall surface of the add-on part 205, as illustrated in FIG. 3. In addition, the foam 305 may be of one foam layer or a plurality of foam layers. Further, in certain embodiments, the capacitive touch sensor 301 may have an integrated chip that has a 16-bit microcontroller to detect touch by measuring the change in the capacitance. The capacitive touch sensor 301 may also detect the relative change of capacitance in the presence of a human finger, and convert the change into a voltage output from high to low. In certain embodiments, the output voltage may range from 1.5 to 2 V.

According to certain embodiments, touch may be an effective tool to input and control the device based on capacitance. Capacitance is an electrical property and represents the amount of charge that a capacitor can hold at a given voltage. Capacitance may be measured in Farad (F) and it may be described in the unit coulomb per volt as: $C=Q/V$, where C is the capacitance in Farad (F), Q is the magnitude of charge stored on each plate (coulomb), and V is the voltage applied to the plates (volts).

Figure 4:
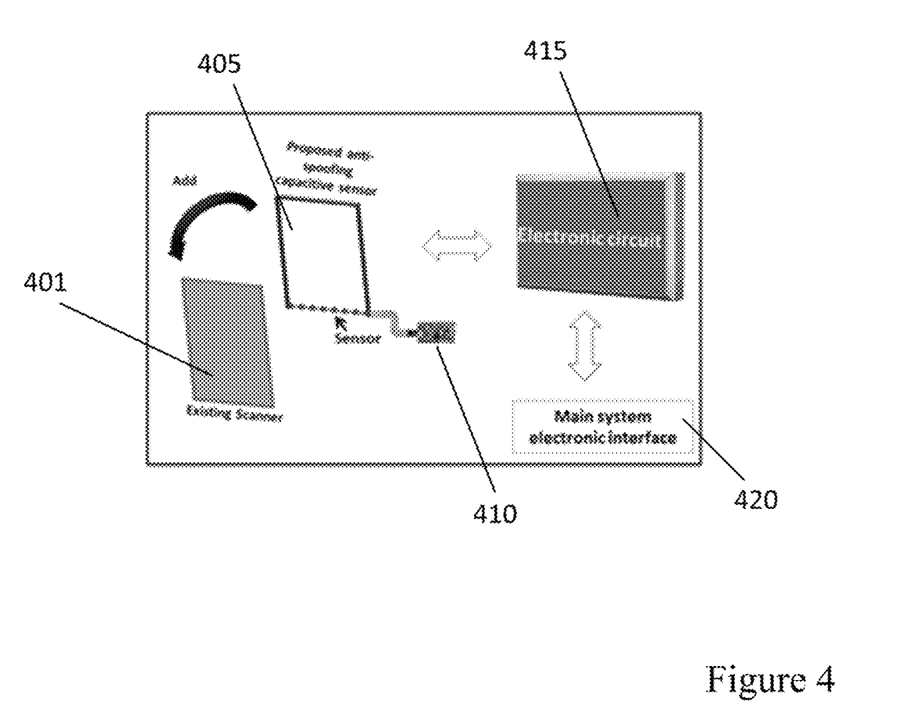
FIG. 4 illustrates a schematic representation of the add-on part according to certain embodiments.

FIG. 4 illustrates a schematic representation of the add-on part to prevent anti-spoofing in existing biometric scanner devices according to certain embodiments. The schematic representation illustrated in FIG. 4 also provides an overview of the system shown in FIGS. 2(A)-2(D) and FIG. 3. For instance, FIG. 4 illustrates that a capacitive sensor 405 may be added or attached to an existing scanner 401 of an existing biometric scanning device or fingerprint scanning device. The capacitive sensor 405 may also include an additional circuit board 410 that may be configured with functionalities for the operation and utilization of the capacitive sensor 405. The combined unit of the capacitive sensor 405 and the existing scanner 401 may be electrically connected to an electronic circuit 415, which may be configured to receive fingerprint information obtained from the capacitive sensor 405 and existing scanner 401. In an embodiment, the electronic circuit 415 may use the fingerprint information received from the capacitive scanner 405 and existing scanner 401 to verify the authenticity of the fingerprint and determine whether or not the scanned fingerprint is from a fake or real finger. Once the fingerprint information has been processed and analyzed at the electronic circuit 415, the results may be outputted to a main system electronic interface 420.

Figure 5:
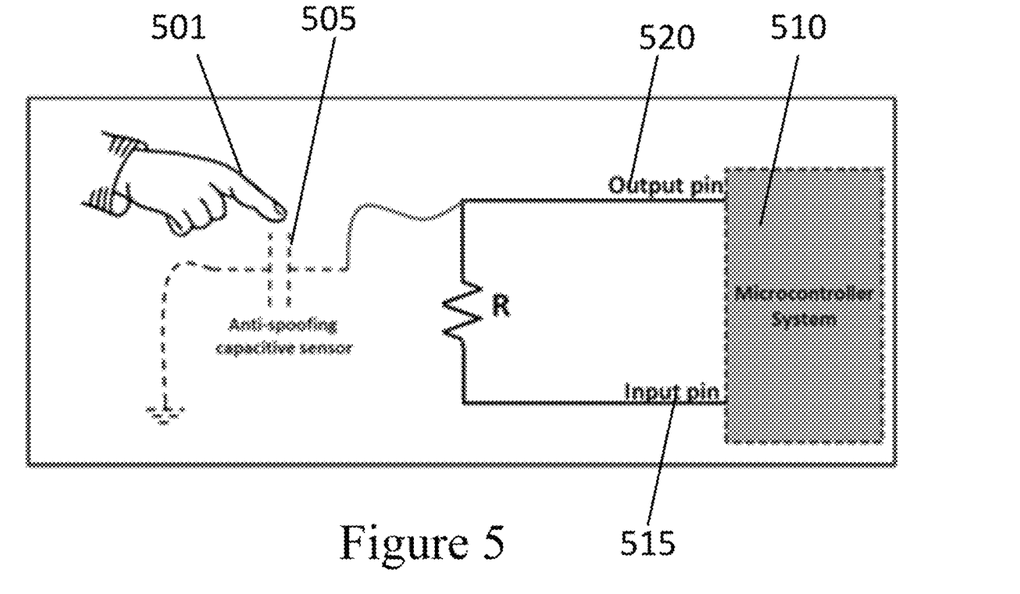
FIG. 5 illustrates an exemplary schematic representation of a mechanism involved in the capacitive sensor according to certain embodiments.

FIG. 5 illustrates an exemplary schematic representation of a mechanism involved in the capacitive sensor according to certain embodiments. As illustrated in FIG. 5, a person's finger 501 may be pressed against a sensor pad of an anti-spoofing capacitive sensor 505, which has functionalities as the capacitive sensor device described herein. Fingerprint information obtained from the anti-spoofing capacitive sensor 505 may be fed to a microcontroller system 510 for processing and analysis of the fingerprint information via an input pin 515. Results of the processing and analysis from the microcontroller system may be sent, via the output pin 520, output a result of the processing and analysis as to whether the finger pressed against the anti-spoofing capacitive sensor 505 is real or fake.

Figure 6:
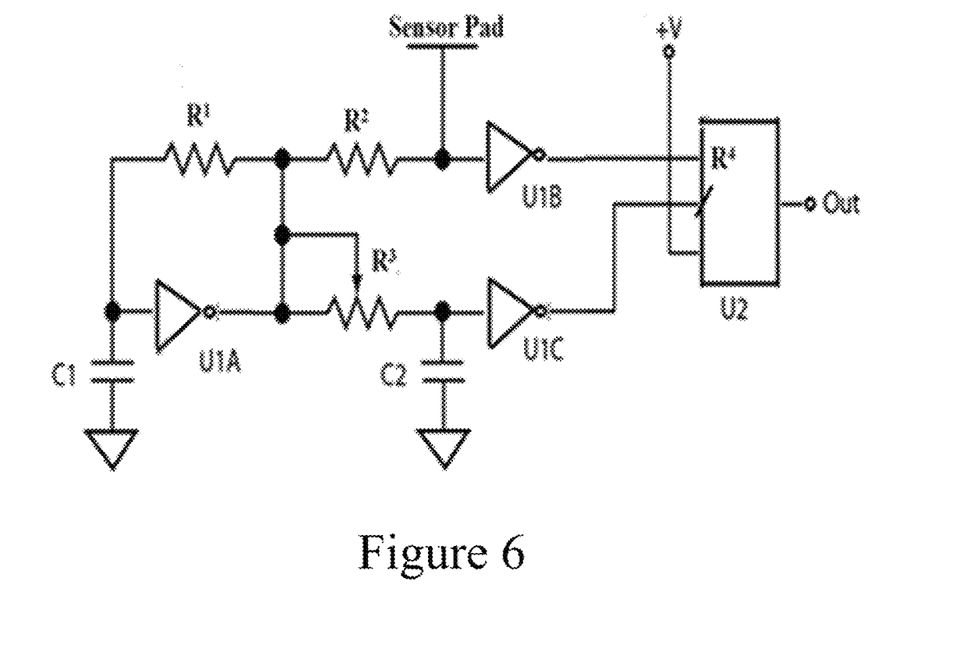
FIG. 6 illustrates a circuit diagram of a mechanism involved in the anti-spoofing capacitive sensor of FIG. 5.

Further, FIG. 6 illustrates a circuit diagram of a mechanism involved in the anti-spoofing capacitive sensor of FIG. 5 according to certain embodiments. In the circuit of FIG. 6, the capacitance between the test plate and earth may be equal to the value of the capacitance C1. At the time when any person moves in the vicinity of the plate, it builds two additional capacitors; one between the sensor and the body, and the other capacitor between the body and the earth. Thus, the resulting total capacitance between the plate and the earth may become larger by the change in capacitance $\Delta C$. This may be reflected by the equation: $C=C1+\Delta C$ . . . .

This type of sensor, according to certain embodiments, may be identified as a capacitive occupancy sensor. Being a conductive medium with a high dielectric constant, the human body develops a coupling capacitance to its surroundings. The coupling capacitance may change due to the presence of the persons in the target area. Based on this capacitance, the system may recognize the presence of human liveliness. Further, using small integrated circuits (ICs) and passive components, the capacitive sensor can yield excellent sensitivity and extremely fast response time. A high-frequency oscillator, inverter U1A together with timing components resistance and capacitance, generate square wave pulses. Thus, output signals may normally remain at logic high and may connect to the biometric device using the microprocessor.

Figure 7:
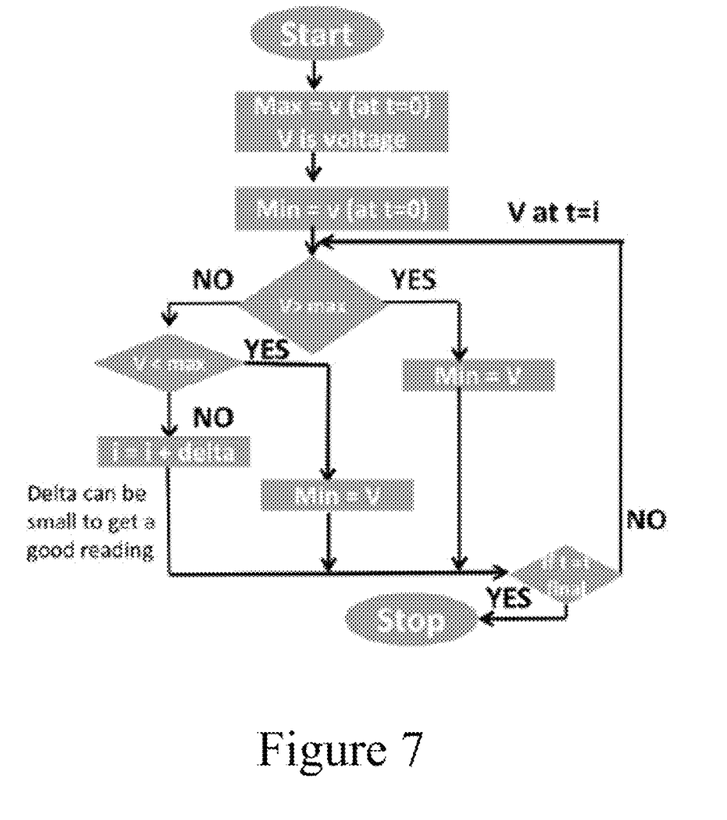
FIG. 7 illustrates an exemplary algorithm for peak detection of a pulse sensor according to certain embodiments.

FIG. 7 illustrates and exemplary flowchart for peak detection of a pulse sensor according to certain embodiments.

Figure 8:
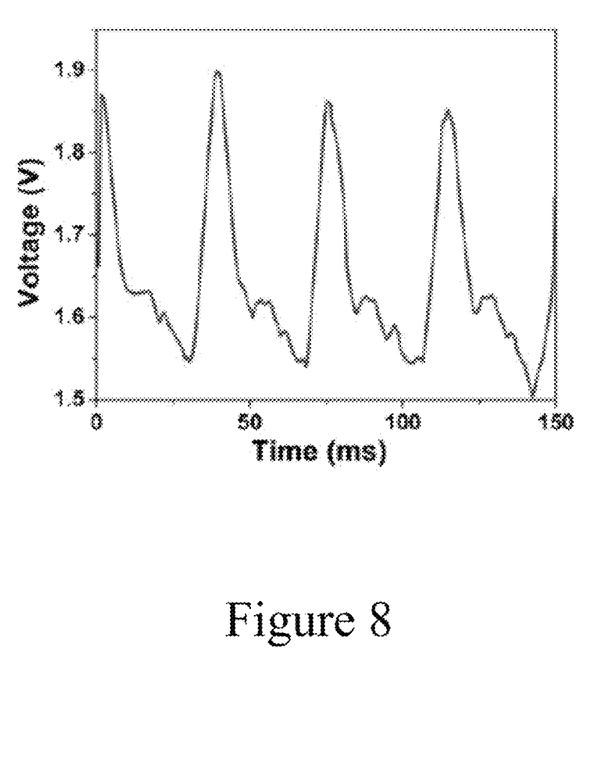
FIG. 8 illustrates a voltage signal from the pulse sensor after modification with a filter with respect to time according to certain embodiments.

FIG. 8 illustrates a voltage signal obtained from the pulse sensor after modification with a filter with respect to time, according to certain embodiments. The microcontroller may be used to obtain the series of readings from the pulse sensor. Further, the readings may be passed through a band-pass filter to remove noise. As illustrated in FIG. 8, an output heartbeat (BPM unit) is represented as a waveform (sawtooth wave) riding on a DC voltage. This is illustrated in FIG. 8 with the y-axis representing the voltage (V) and x-axis representing the time (ms). The difference in voltage between the power to the pulse sensor (3.3V) and the voltage with reference to the Arduino (5V) were checked. The average values of heartbeat (BPM) were correlated with the values, and the average voltage (mV) difference obtained was about 0.5 V.

Experimental Procedure

An artificial finger was fabricated using silicone rubber. The device was randomly tested with the subjects' fingers and the artificial finger. For each test, the device's scanning area was cleaned to remove dust and fingerprint smudges. Then, the finger (human or artificial) was placed on the scanner. If the fingerprint scanner detects a finger within 5 seconds, the test is registered as a successful detection. If 5 seconds passed and the scanner does not detect a finger, the test is registered as an unsuccessful detection.

According to certain embodiments, the capacitive sensor and pulse sensor can be used to determine if the finger is real or fake based on certain capacitance and pulse thresholds. For example, in an embodiment, the capacitance of the human skin lies in the range of about 0.02 to $0.06/F/cm^2$, and the pulse sensor voltage difference lies in the range of about 0.2-0.5 V. In other embodiments, the threshold ranges of the capacitance and pulse may each be preset in the code for detection. In certain embodiments, biometric information of the user may first be obtained and stored into the device so that in future uses, the device may determine whether the information obtained from the scanned finger matches the information previously stored.

Results

According to certain embodiments, the accuracy for detecting the human finger was found to be approximately 97.2%, while the success rate for the artificial finger was found to be approximately 100%. The overall success rate was approximately 99.6%. The results of the tested subjects are summarized in Table 1. The device never registered an artificial finger as a human finger (false positive) since the fake fingers do not have capacitance and pulses. In addition, the processing time for peak detection was recorded to be 0.28 seconds. From these results, it can be seen that the peak detector according to certain embodiments may provide for short processing times. In addition, the operating environmental conditions may have a significant effect on the measured success rate values. The varying magnitude of pressure applied and the sliding of the finger on the scanner may also affect results. However, the limitations from standard biometric devices may be overcome by including multiple sensor information for establishing high security to biometric devices.

TABLE I

A SUMMARY OF RESULTS FOR THE ANTI-SPOOFING DEVICE

| Test type | Success rate (%) |
| --- | --- |
| Artificial and human finger (312 tests) | 99.6 |
| Artificial finger (94 tests) | 100 |
| Human finger (218 tests) | 97.2 |

Figure 9:
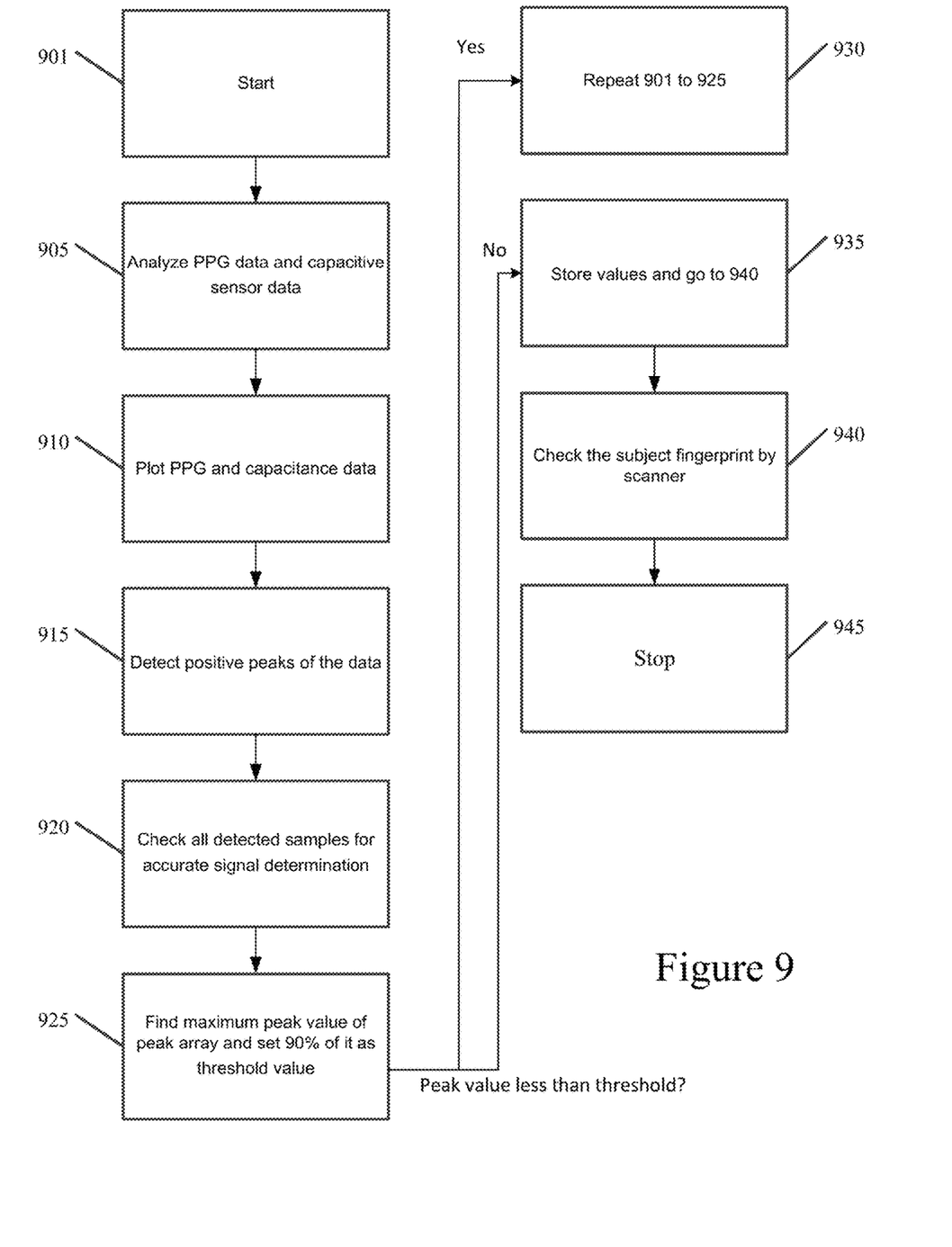
FIG. 9 illustrates a method according to certain embodiments.

FIG. 9 illustrates a method according to certain embodiments. In particular, the FIG. 9 illustrates a method for the add-on part according to certain embodiments. The method may begin at 901. At 905, the method may include analyzing the PPG data and capacitive sensor data. At 910, the method may include plotting the PPG and capacitance data. In addition, at 915, the method may include detecting positive peaks of the data by comparing three successive measurements on the samples. Further, at 920, the method may include checking all detected samples for accurate signal determination. At 925, the method may include finding the maximum peak value of the peak array, and setting 90% of it as a threshold value. At 930, if the peak value is less than the threshold, the method may include repeating 901 to 925. However, at 935, if the peak value is greater than the threshold, the method may include storing the values and proceeding to 940. In particular, at 940, the method may include checking the subject fingerprint by the scanner. Finally, at 945, the method ceases.

Figure 10:
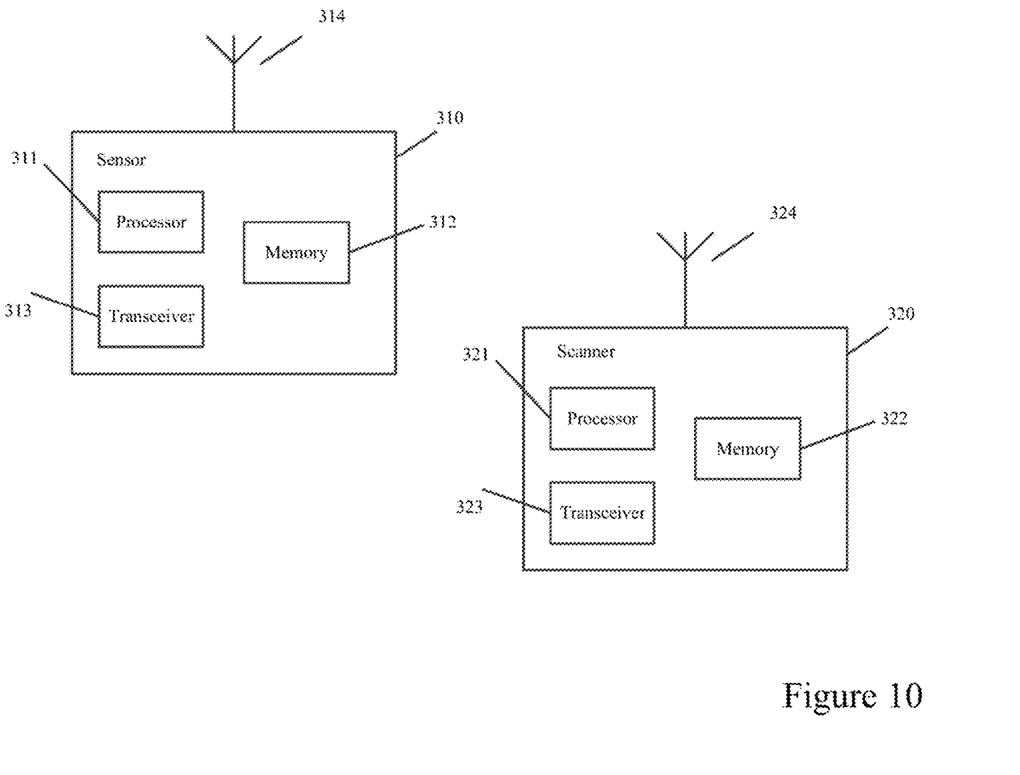
FIG. 10 illustrates a system according to certain embodiments.

FIG. 10 illustrates a system according to certain embodiments. It should be understood that the contents of FIGS. 1-9 may be implemented by various means or their combinations, such as hardware, software, firmware, one or more processors and/or circuitry. In one embodiment, a system may include several devices, such as, for example, a sensor 310 and/or a scanner 320. The system may include more than one sensor 310 such as any of the sensors described herein, and more than one scanner 320.

The sensor 310 and scanner 320 may each include at least one processor 311 and 321. At least one memory may be provided in each device, and indicated as 312 and 322, respectively. The memory may include computer program instructions or computer code contained therein. One or more transceivers 313 and 323 may be provided, and each device may also include an antenna, an antenna respectively illustrated as 314 and 324. Although only one antenna each is shown, many antennas and multiple antenna elements may be provided to each of the devices. Other configurations of these devices, for example, may be provided. For example, sensor 310 and scanner 320 may be additionally configured for wired communication, in addition to wireless communication, and in such a case antennas 314 and 324 may illustrate any form of communication hardware, without being limited to merely an antenna.

Transceivers 313 and 323 may each, independently, be a transmitter, a receiver, or both a transmitter and a receiver, or a unit or device that may be configured both for transmission and reception. Further, one or more functionalities may also be implemented as virtual application(s) in software that can run on a server.

In some embodiments, an apparatus, such as the sensor 310 or scanner 320, may include means for carrying out embodiments described above in relation to FIGS. 1-9. In certain embodiments, at least one memory including computer program code can be configured to, with the at least one processor, cause the apparatus at least to perform any of the processes described herein.

Processors 311 and 321 may be embodied by any computational or data processing device, such as a central processing unit (CPU), digital signal processor (DSP), application specific integrated circuit (ASIC), programmable logic device (PLDs), field programmable gate arrays (FPGAs), digitally enhanced circuits, or comparable device or a combination thereof. The processors may be implemented as a single controller, or a plurality of controllers or processors.

For firmware or software, the implementation may include modules or unit of at least one chip set (for example, procedures, functions, and so on). Memories 312 and 322 may independently be any suitable storage device such as those described above. The memory and the computer program instructions may be configured, with the processor for the particular device, to cause a hardware apparatus such as sensor 310 or scanner 320, to perform any of the processes described above (see, for example, FIGS. 1-9). Therefore, in certain embodiments, a non-transitory computer-readable medium may be encoded with computer instructions or one or more computer program (such as added or updated software routine, applet or macro) that, when executed in hardware, may perform a process such as one of the processes described herein. Alternatively, certain embodiments may be performed entirely in hardware.

According to other embodiments, it may further be possible to provide the best set of operators to be searched. In addition, with the right blend of non-linear operators, POPs may learn very complex problems that cannot be learned by deeper and more complex MLPs. In other embodiments, GOPs and POPs may conveniently be used in any application where any other classifier (e.g., ANNs, SVMs, RF, etc.) is used.

Although the foregoing description is directed to the preferred embodiments of the invention, it is noted that other variation and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. An anti-spoofing method, comprising:
    measuring, with an add-on part comprising a photoplethysmography (PPG) sensor and a capacitance sensor, PPG data and capacitance data of an object;
    with the PPG data and the capacitance data, detecting, by a microprocessor, positive peaks of the PPG data and the capacitance data by comparing successive measurements;
    finding, by the microprocessor, a maximum peak value of the detected positive peaks;
    generating, by the microprocessor, a threshold value based on the detected positive peaks;
    if the maximum peak value is greater than the threshold value, analyzing, by the microprocessor, a fingerprint of the object;
    determining, by the microprocessor, based on the PPG data, the capacitance data and the fingerprint of the object, at least one of if the object is authorized or unauthorized, and if the object is a human being or not a human being;
    checking all of the detected positive peaks for accurate signal determination; and
    plotting the PPG data and capacitance data,
    wherein if the maximum peak value is less than the threshold value, the method further comprises repeating the plotting the PPG data and the capacitance data, detecting positive peaks of the data, checking all of the detected positive peaks, finding the maximum peak value, and generating the threshold value.

2. The method of claim 1, further comprising detecting, with the capacitance sensor, touch of the object by measuring a change of capacitance of the object.

3. The method of claim 2, further comprising converting, by the microprocessor, the change of capacitance of the object into a voltage output.

4. A computer program, embodied on a non-transitory computer readable medium, the computer program, when executed by a processor, causes the processor to:
    measure photoplethysmography (PPG) data and capacitance data of an object;
    with the PPG data and the capacitance data, detect positive peaks of the PPG data and the capacitance data by comparing successive measurements;
    find a maximum peak value of the detected positive peaks;
    generate a threshold value based on detected the positive peaks;
    if the maximum peak value greater than the threshold value, analyze, by the microprocessor, a fingerprint of the object;
    determine, by the microprocessor, based on the PPG data, the capacitance data and the fingerprint of the object, at least one of if the object is authorized or unauthorized, and if the object is a human being or not a human being;
    check all of the detected positive peaks for accurate signal determination; and
    plot the PPG data and capacitance data,
    wherein if the maximum peak value is less than the threshold value, the computer program, when executed by a processor, further causes the processor to repeat the plotting the PPG data and the capacitance data, detecting positive peaks of the data, checking all of the detected positive peaks, finding the maximum peak value, and generating the threshold value.

5. The computer program of claim 4, wherein the computer program, when executed by a processor, further causes the processor to detect a touch of the object by measuring a change of capacitance of the object.

6. The computer program of claim 5, wherein the computer program, when executed by a processor, further causes the processor to convert the change of capacitance of the object into a voltage output.

7. An apparatus, comprising:
    a processor; and
    a memory including computer program code,
    wherein the memory and the computer program code are configured to, with the processor, cause the apparatus at least to:
    receive photoplethysmography (PPG) data and capacitance data from an add-on part;
    with the PPG data and the capacitance data, detect positive peaks of the PPG data and the capacitance data by comparing successive measurements;
    find a maximum peak value of the detected positive peaks;
    generate a threshold value based on the detected positive peaks;
    if the maximum peak value is greater than the threshold value, analyze a fingerprint of the object;
    determine, based on the PPG data, the capacitance data and the fingerprint of the object, at least one of if the object is authorized or unauthorized, and if the object is a human being or not a human being;
    check all of the detected positive peaks for accurate signal determination; and
    plot the PPG data and capacitance data,
    wherein if the maximum peak value is less than the threshold value, the computer program, when executed by a processor, further causes the processor to repeat the plotting the PPG data and the capacitance data, detecting positive peaks of the data, checking all of the detected positive peaks, finding the maximum peak value, and generating the threshold value.

8. The apparatus of claim 7, wherein the memory and the computer program code are configured to, with the processor, cause the apparatus to convert a change of capacitance of the object into a voltage output.

* * * * *